United States Patent [19]

Kanda et al.

[11] 4,044,273
[45] Aug. 23, 1977

[54] ULTRASONIC TRANSDUCER

[75] Inventors: Hiroshi Kanda, Tokorozawa; Kageyoshi Katakura, Naka; Takaji Suzuki, Kashiwa, all of Japan

[73] Assignees: Hitachi, Ltd.; Hitachi Medical Corporation, both of Japan

[21] Appl. No.: 635,086

[22] Filed: Nov. 25, 1975

[30] Foreign Application Priority Data

Nov. 25, 1974 Japan .............................. 49-134311

[51] Int. Cl.² .......................................... H01L 41/04
[52] U.S. Cl. .................................... 310/313; 310/335; 340/9; 340/8 FT
[58] Field of Search ................. 310/8.1, 8.2, 8.3, 8.7, 310/9.5, 9.6; 350/211, 199; 181/176; 340/8 MM, 8 FT, 8 L, 8 S, 8 R, 9, 10

[56] References Cited

U.S. PATENT DOCUMENTS

| | | | |
|---|---|---|---|
| 711,974 | 10/1902 | Hyde | 181/176 |
| 2,831,785 | 4/1958 | Kearney | 340/10 X |
| 2,855,526 | 10/1958 | Jones | 310/8.5 |
| 3,020,395 | 2/1962 | Peltz | 350/211 X |
| 3,162,766 | 12/1964 | Ploke | 350/211 |
| 3,166,730 | 1/1965 | Brown, Jr. et al. | 340/10 |
| 3,433,461 | 3/1969 | Scarpa | 310/8.2 X |
| 3,903,990 | 9/1975 | Tannaka | 340/8 L |
| 3,965,455 | 6/1976 | Hurwitz | 310/8.2 |

*Primary Examiner*—Mark O. Budd
*Attorney, Agent, or Firm*—Craig & Antonelli

[57] ABSTRACT

A transducer included in an ultrasonic source is a concave ultrasonic transducer made of a piezoelectric material. The concave ultrasonic transducer is shaped into such body of revolution that a section of the transducer forms a revolutionary arc surface consisting of two arcs. Owing to the shape, an ultrasonic source similar to a conventional ring type source is constructed.

16 Claim, 14 Drawing Figures

FIG. 1
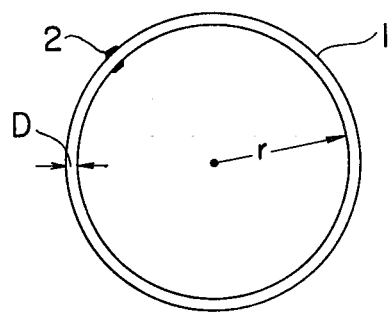
FIG. 2B                  FIG. 2A
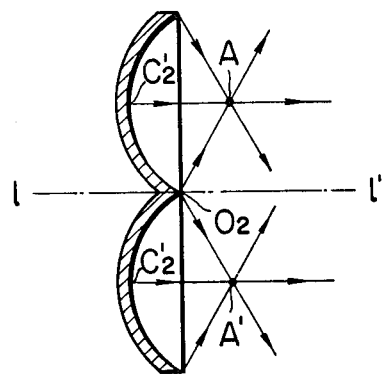     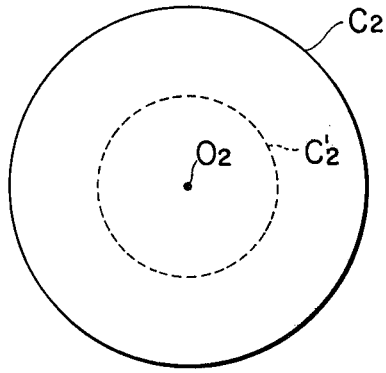
FIG. 3B                  FIG. 3A
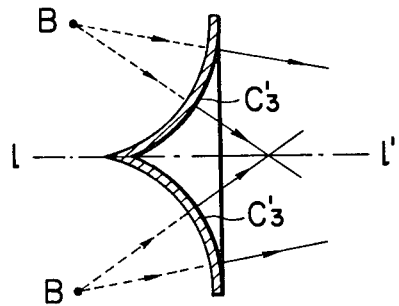     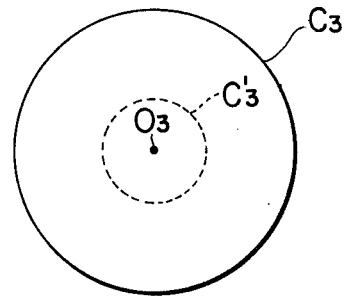

ULTRASONIC TRANSDUCER

BACKGROUND OF THE INVENTION

1. Field of the Invention

This invention relates to an ultrasonic transducer, and more particularly to an ultrasonic source which can form a fine ultrasonic beam over a comparatively extensive scope in a predetermined medium.

2. Description of the Prior Art

In an ultrasonic transducer (as to which it is generally well known that an ultrasonic source is used also as a receiver for receiving reflected waves) having hitherto been employed in, for example, a diagnostic ultrasound equipment, a fine beam with a beam width of about 1 - 3 mm need be obtained in a comparatively extensive scope of about 1 - 30 cm in the interior of the body, in other words, at a depth of about 1 - 30 cm. The reason therefor is that the resolution depends upon the beam width and that a smaller beam width can achieve a higher resolution. As an expedient, it has been proposed to use a ring type transducer for the ultrasonic source.

FIG. 1 shows a plan view of the ring type transducer. In the figure, numeral 1 designates the ring type transducer power, while numeral 2 denotes an electrode disposed in any desired place of the transducer proper 1. The transducer proper 1 employs, for example, lead titanate zirconate as a piezoelectric material. By sintering the material in a conventional way, the ring is shaped by way of example into a radius $r$ of 10 cm and a width D of 1 mm.

Upon condition that the width (D) of the ring is sufficiently smaller than the diameter ($2r$) of the transducer (for example, the magnitudes $r$ and D are set at the above-mentioned values), all the wave fronts which arrive at points on the axis of the transducer from the ring-shaped transducer proper are in phase and hence, the wave fronts are intensified with one another by constructive interference. In contrast, at points other than those on the axis of the transducer, the arriving wave fronts have phases which are mutually different, and hence, they are canceled from one another by destructive interference. In consequence, the ring type transducer can form a fine ultrasonic beam along the axis thereof. Accordingly, the ultrasonic source which employs the ring type transducer is suitable for generating ultrasonic waves of small beam width. Thus, as regards the directivity, the ring type transducer is far more excellent than a prior-art transducer of the surface type (flat disk, curved or concave disk).

The ring type transducer, however, has the following disadvantages as compared with the surface type transducer and has scarcely been put into practical use up to now. (1) On account of attenuation resulting from to the spherical spread, the sensitivity is conspicuously insufficient at a large depth. (2) In case where ultrasonic waves are transmitted into a medium and where reflected waves are received, a paste is interposed between the transducer and the medium. When the contact of the transducer with the medium is poor on account of the existence of air bubbles etc. in the paste, the directivity of the beam is disturbed. (3) The amplitude of a side lobe is large.

SUMMARY OF THE INVENTION

It is an object of this invention to provide an ultrasonic source or ultrasonic transducer which is free from the disadvantages of the ring type transducer, and yet, which exhibits an excellent directivity as in the ring type source.

In order to accomplish such object, this invention adopts a surface type transducer or a combination between a surface type transducer and an acoustic lens, and realizes an ultrasonic source equivalent to the ultrasonic source employing the ring type transducer. More specifically, according to this invention, the wave fronts of ultrasonic waves generated from the surface type transducer are caused to converge in front of or behind the surface type transducer. Thus, wave fronts which arise from the points of convergence form the same directivity as that of the wave fronts of ultrasonic waves generated from the prior-art ring type transducer.

BRIEF DESCRIPTION OF THE DRAWING

FIG. 1 is a view of a ring type transducer which is used in a prior-art ultrasonic source, FIGS. 2A and 2B are a plan view and a sectional view of a surface type transducer which is used in an ultrasonic source of this invention, respectively, FIGS. 3A and 3B are a plan view and a sectional view of another surface type transducer which is used in the ultrasonic source of this invention, respectively.

DESCRIPTION OF THE PREFERRED EMBODIMENTS

Figure 4:
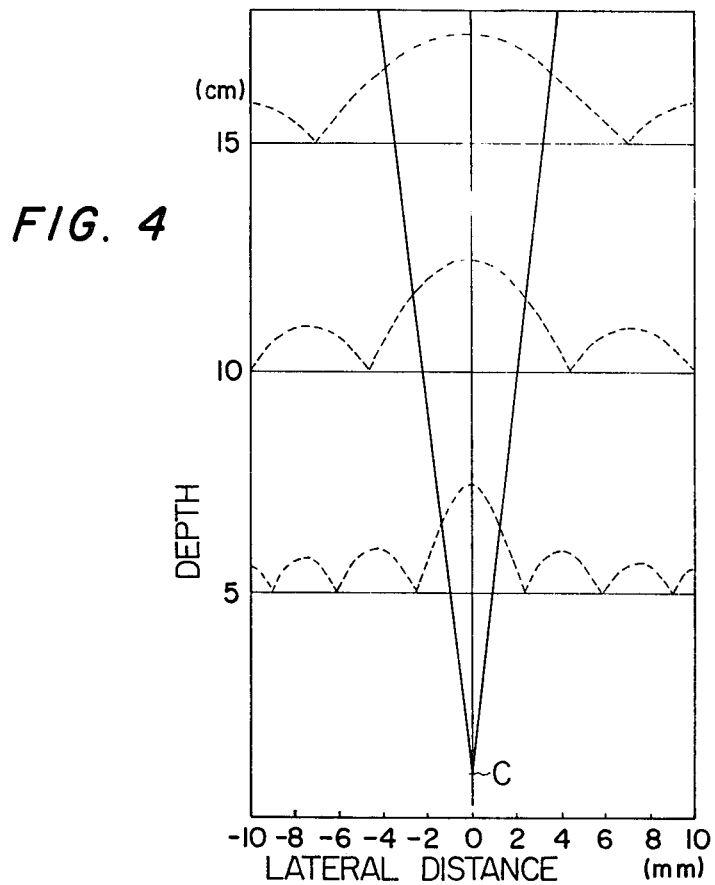
FIG. 4 is a characteristic curve diagram of the embodiment of this invention illustrated in FIGS. 2A and 2B, FIGS. 5 and 6 are views each showing an embodiment in which an acoustic lens is coupled to the surface type transducer.

FIG. 2A is a plan view which shows a concave transducer as a surface type transducer constituting the ultrasonic source of this invention. In the figure, a point $O_2$ is the central point of a circle $C_2$, and a circle $C_2'$ of a dotted line denotes the lowermost part of the front surface of the circle $C_2$. FIG. 2B is a sectional view in which the concave transducer shown by the plan view of FIG. 2A is cut along an arbitrary plane containing the central point $O_2$. As apparent from these figures, in the concave transducer, the level of the surface (with respect to the circular portion $C_2'$) becomes lower as the distance from the central point $O_2$ comes closer to the part of the circle $C_2'$, the level becomes the lowest at the part of the circle $C_2'$, the level becomes higher as the distance from the part of the circle $C_2'$ comes closer to the circumference of the circle $C_2$, and the level becomes the highest (the same level as that of the central point $O_2$) at the part of the circumference. In other words, the concave transducer has a protrusion (whose level is equal to that of the circumferential portion) at the part of the central point $O_2$. It can be said that, as shown in FIG. 2B, the concave transducer is shaped into such body of revolution that the section of the transducer containing its axis forms a revolutionary arc surface consisting of two adjacent concave arcs. In FIG. 2B, $l - l'$ indicates the axis of the transducer, and A and A' represent the centers of curvature of the respective concave arcs. The locus of the centers of curvature forms a ring in frount of the front surface of the concave transducer (arrows in the figure are directed onto the front surface side, or the right side of the concave arcs as viewed in the figure is the front surface side), the ring having the line $l - l'$ as its axis and passing through the centers of curvature A and A'.

According to such concave transducer, ultrasonic waves which are generated from the front surface of the transducer converge to the centers of curvature A and A'. Consequently, wave fronts which are transmitted from a source composed of the centers of curvature are effectively the same as wave fronts arising from a ring type transducer. In other words, the ultrasonic source employing the above concave surface type transducer produces an ultrasonic beam equivalent to that of an ultrasonic source employing the ring type transducer.

The concave transducer shown in FIG. 2A is formed into the predetermined shape by sintering with lead titanate zirconate, its thickness indicated by the section in FIG. 2B is 1 mm, and it generates ultrasonic waves of frequencies up to 5 MHz.

Further, the surface type transducer for the ultrasonic source according to this invention may be one which is obtained in such way that a piezoelectric material being hitherto well known, for example, lead titanate zirconate (PZT), quartz, lithium sulphate ($LiSO_4$), lithium niobate ($LiNbO_3$) or the like is molded into a predetermined shape and that metal electrodes of gold or the like are formed on both the surfaces of the molded compact.

FIG. 3A is a plan view which shows a convex transducer as a surface type transducer constituting the ultrasonic source of this invention. In the figure, $O_3$ is the central point of a circle $C_3$, and a circle $C_3'$ indicated by a dotted line represents a part of the surface which is lower in level than the circumference of the circle $C_3$. FIG. 3B is a sectional view in which the convex transducer shown in FIG. 3A is cut along an arbitrary plane containing the central point $O_3$. In FIG. 3B, a straight line $l - l'$ denotes the axis of the transducer, while points B and B' denote the centers of curvature of respective convex arcs. As seen from both the figures, in the convex transducer, the level becomes lower gradually from the circumference towards the central point $O_3$ in the front surface. The tendency of the lowering of the level defines the convex arcs as shown by the section of FIG. 3B. A part of the surface indicates by points $C_3'$ of the convex arcs corresponds to the part indicated by the circle of the dotted line $C_3'$ in FIG. 3A. In other words, the convex transducer is shaped into such body of revolution that the section of the transducer containing its axis forms a revolutionary arc surface consisting of two adjacent convex arcs. Consequently, the locus of the centers of curvature B and B' of the revolutionary arc surface at the back surface side (arrows in the figure are directed onto the front surface side) of the convex surface type transducer forms a ring behind the back surface, the ring having the line $l - l'$ as its axis and passing through the points B and B'.

According to such convex transducer, ultrasonic waves which are generated from the front surface propagate as if they were transmitted from the centers of curvature B and B'. Effectively, therefore, the ultrasonic beam which is generated from the ring type transducer of the prior art is realized. That is, the ultrasonic source employing the above convex transducer becomes one equivalent to the ultrasonic source employing the ring type transducer.

The transducer shown in FIG. 3A is formed into the predetermined shape by sintering with the same material as that of the transducer illustrated in FIG. 2A, its thickness of the section is also 1 mm, and the frequencies to be generated are the same.

Although electrodes are omitted in the transducers of FIG. 2A and FIG. 3A, they may be disposed above and below the circumferential part.

The inventors have confirmed from theoretical characteristic curves in FIG. 4 that the source employing the surface type transducer stated above is equivalent to the source employing the prior-art ring type transducer. More specifically, FIG. 4 illustrates beam widths (the beam width is defined to be a width at which the sound pressure lowers by $-3$ dB with reference to a sound pressure on the axis of the transducer) and sound pressure distributions (indicated by broken lines) in the lateral direction at representative depths at the time when, by way of example, the diameter of the transducer is set at 20 mm, the radius of curvature of the arc surface at 9 mm and the ultrasonic frequency at 2.25 MHz in the case of the source employing the concave surface type transducer shown in FIG. 2A. In FIG. 4, the axis of abscissas indicates the lateral direction, while the axis of ordinates denotes the depth direction. It is understood from the figure that the effective or virtual ring type source appears at a point C, the ultrasonic waves being seen as if they were transmitted from this point, and that a narrow main beam (indicated by solid lines) is formed along the axis of the transducer.

Figure 5:
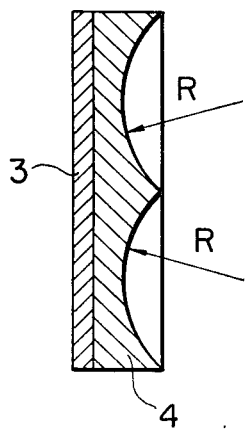
Figure 6:
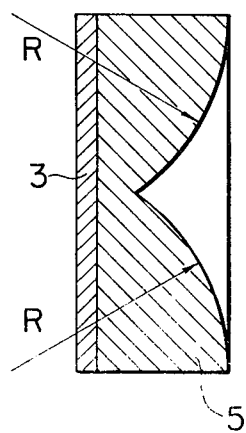

FIGS. 5 and 6 are sectional views which show combinations of a flat disk transducer and an acoustic lens disposed on a surface thereof, the combinations being capable of providing ultrasonic sources adapted to operate quite similarly to the sources employing the foregoing transducers of FIGS. 2A and 3A, respectively. In FIG. 5, numeral 3 designates a plane transducer, being a surface type transducer, whose both surfaces are flat. Numeral 4 denotes an acoustic lens, one surface of which is flat and the other surface of which is the same revolutionary arc surface as in FIG. 2B. One surface of the plane transducer 3 and the flat surface of the acoustic lens 4 are bonded together.

Regarding the material of the acoustic lens 4, the speed of sound in the material need be higher than the speed of sound in a medium in which acoustic waves are to be propagated. For this reason, there are usually used aluminum, brass, nickel, acryl resins, bakelite, etc. It is well known that these materials can be worked into surfaces of predetermined shapes.

In case of FIG. 5, ultrasonic plane waves generated from the flat disk transducer 3 become, after passing through the acoustic lens 4, the same wave fronts as those which are obtained by the transducer illustrated in FIGS. 2A and 2B. Therefore, for the same reason as explained in connection with FIGS. 2A and 2B, an effective ring type source is formed in front of the acoustic lens 4.

In FIG. 6, numeral 3 represents the same flat disk transducer as shown in FIG. 5, and numeral 5 denotes an acoustic lens whose one surface is flat and whose other surface is the same revolutionary arc surface as in FIG. 3B. The flat surfaces of the disk transducer 3 and the acoustic lens 5 are bonded to each other.

Also in case of FIG. 6, for the same reason as stated above, an ultrasonic beam has under the action of the acoustic lens 5 the same wave fronts as those which are obtained by the transducer shown in FIGS. 3A and 3B. Therefore, the same source as that employing the ring type transducer can be realized.

In FIGS. 5 and 6, arrows denoted by R indicate the directions of the centers of curvature of the respective acoustic lenses.

It has been experimentally verified by the inventors that the ultrasonic sources employing the transducers shown in FIGS. 5 and 6 are effectively the same as the source employing the prior-art ring type transducer.

Figure 7:
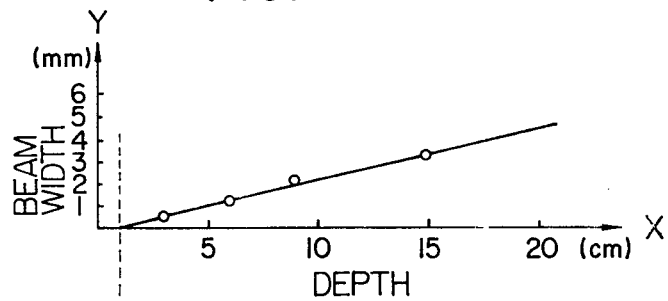
FIG. 7 is a characteristic curve diagram of the embodiment of this invention illustrated in FIG. 5.

FIG. 7 illustrates an example of actual measurement data based on this experiment. The data are of the source which employs the tansducer and the acoustic lens shown in FIG. 5. The experiment was carried out as follows. A flat disk transducer was used for providing a frequency of 2 MHz, which has a diameter of 20 mm and which was made of a PZT material. Bonded onto the surface of the transducer was an acoustic lens which had a diameter of 20 mm and an arc radius of curvature of 5 mm and which was made of an acryl resin. Water was used as the medium. In the graph of FIG. 7, the X-axis indicates the direction of transmitting ultrasonic waves, while the Y-axis indicates the lateral direction. Marks o denote actually measured values, and the solid line represents a theoretical curve. As apparent from the figure, the directivity exhibits a small beam width, and a ring type source is generated at a position of the dotted line.

Figure 8:
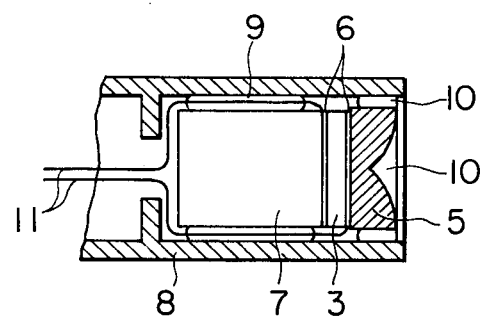
FIG. 8 is a view showing a practical apparatus of the embodiment illustrated in FIG. 6.

FIG. 8 shows a concrete apparatus which was used for actually measuring the directivity of the ultrasonic source employing the combination of the flat disk transducer and the acoustic lens shown in FIG. 6. (The ultrasonic source employing the combination of the transducer and the lens shown in FIG. 5 as was used for obtaining the directivity in FIG. 7 was constructed in a like manner to the apparatus shown in FIG. 8 and merely differed in the transducer and the lens.)

Referring to FIG. 8, numeral 3 designates a flat disk ultrasonic transducer having a frequency of 5 MHz which is made of PZT and which has a diameter of 20 mm. Silver electrodes 6 are disposed on the front and back surfaces of the transducer 3. Shown at 5 is an acoustic lens of aluminum which has the same shape as in FIG. 6 and which is 20 mm in the diameter and 26 mm in the radius of curvature of the arc. A backing member 7 is made of composite material vinyl chloride containing a tungsten powder. The backing member 7, the transducer 3 and the acoustic lens 5 are bonded together by a bonding agent, and they are housed in a metal case 8 with the acoustic lens 5 facing an open end of the case. The backing member 7 is bonded and fixed to an inner wall of the case 8 by a bonding agent 9. A coating material 10 made of an epoxy resin containing a tungsten powder is applied to the opened part of the case 8, to fill up the concave portion of the acoustic lens 5 to make it smooth and also to fill up the clearance between the lens 5 and the case 8. Shown at 11 are lead wires which are connected to the electrodes 6 of the transducer 3.

Figure 9:
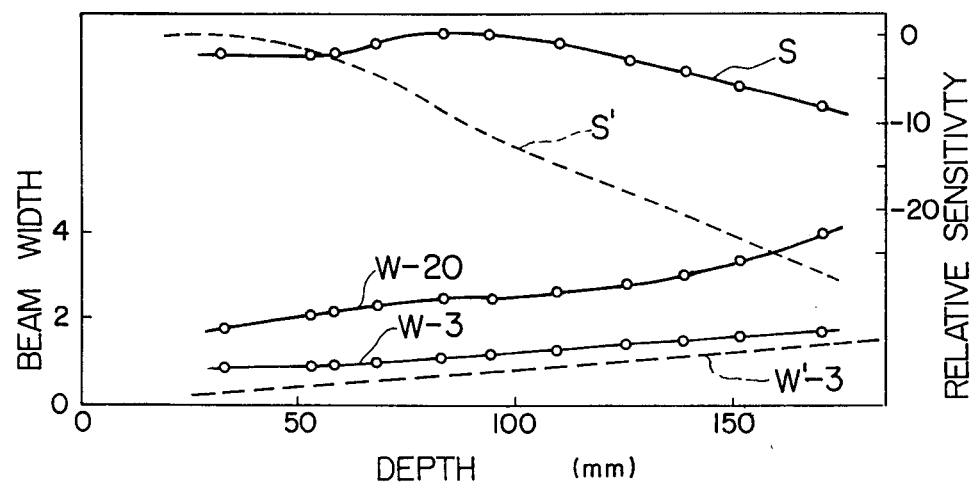
FIG. 9 is a characteristic curve diagram of the apparatus shown in FIG. 8, FIGS. 10A and 10B are views each showing the construction of another embodiment of this invention.

Experimental results obtained by executing the actual measurement of the directivity in the water by the use of such apparatus are illustrated in FIG. 9 together with the directivity of an ultrasonic source employing the prior-art ring type transducer. In the figure, the beam width and the relative sensitivity are taken on the axes of ordinates, respectively, while the depth is taken on the axis of abscissas. Curves W-3 and W-20 represent main beam widths at which the sound pressure lowers by $-3$ dB and $-20$ dB, respectively, and a curve S indicates the relative sensitivity. A curve $W'$-3 represents a main beam width at which the sound pressure of an ultrasonic beam from the source employing the prior-art ring type transducer lowers by $-3$ dB, and a curve $S'$ indicates the relative sensitivity of the prior-art source. The ring type transducer is one for 5 MHz which is molded into a radius of 10 mm and a ring width of 1 mm by using PZT as its material.

As apparent from FIG. 9, the main beam width along the axis in the apparatus of FIG. 8 (the beam width shown by the curve W-3) exhibits values 0.9, 1.3 and 1.6 mm at depths 5, 10 and 15 cm, respectively. On the other hand, the beam width shown by the curve $W'$-3 exhibits values 0.6, 0.9 and 1.1 mm at the depths 5, 10 and 15 cm, respectively. The ultrasonic source of this invention is somewhat inferior in point of narrowness of the beam width, but the beam width to such extent is satisfactory for practical use. The height of a side lobe departing from the axis is $-40$ dB at the maximum in the apparatus of FIG. 8, whereas it is $-16$ dB at the maximum in a source employing a ring type transducer having hitherto been published, so that it is improved to 1/20 by the present invention. This means that, owing to the use of the surface type transducer, the ultrasonic source according to the present invention has succeeded in shortening of the ultrasonic pulse by the acoustic backing (in other words, in widening the band). The spread attenuation of acoustic waves is $-1$ dB/cm in the apparatus of FIG. 8, and is $-2$ dB/cm in the ultrasonic source employing the ring type transducer. With the source employing the surface type transducer as in the present invention, the spread attenuation is improved by 20 dB at a place 20 cm deep. The improvement is based on the following reason. In case of the ring type transducer, the spread of acoustic waves is the spherical spread, and hence, the distance directly affects the attenuation of acoustic waves due to the spread. In contrast, in case of this invention employing the surface type transducer, the spread is the cylindrical one, and hence, the square root of the distance influences the attenuation of acoustic waves due to the spread.

As described above, since this invention uses the surface type transducer as the ultrasonic source, improvements are made in the two points of the side lobe and the spread attenuation. Without these improvements, the source employing the ring type transducer is not useful in practice. This invention makes improvements in the two points at some sacrifice of the beam width, and can realize the ultrasonic source fit for practical use. According to the ultrasonic source of the invention, an ultrasonic transducer whose depth of practical use ranges from about 2.5 cm to about 20 cm has become feasible.

In addition to the above-mentioned effects achieved by this invention, the following effects are accomplished on the basis of the fact that the ultrasonic source is constructed of the surface type transducer in the present invention. In the ultrasonic source of this invention, the whole area of the surface type transducer is used and the ultrasonic waves can be confined into a cylinder about the axis as determined by the diameter of the transducer, over the whole depth as required, so that the spread attenuation of the sound pressure of the ultrasonic beam can be made much less than in the ring type transducer. Since the transducer is of the surface type, the contact area with a medium is large, so that the disturbance of the beam caused by a poor contact can be made much less. Where the concave or convex transducer is employed as the surface type transducer, the width of the ultrasonic beam is determined by the ratio between the acoustic wave and the diameter of the ring defined by the locus of the centers of curvature of the surface, and it is not directly dependent upon the diameter which the transducer itself has, so that the beam width can be changed by varying the curvature of the arc of the concave or convex transducer.

Although only the arc has been referred to in the previous description, it is a matter of course that similar effects can be achieved by the use of curved surfaces approximate to the arc, such as paraboloid and ellipsoid which have the centers of curvature in a like manner to the arc.

Figure 10B:
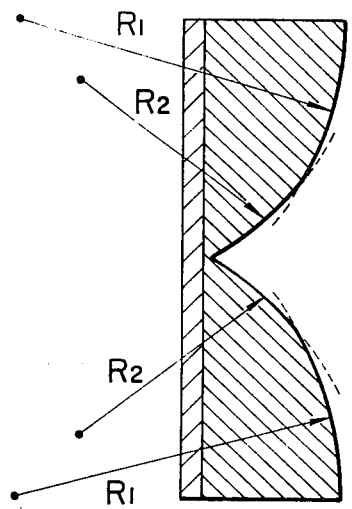
Figure 10A:
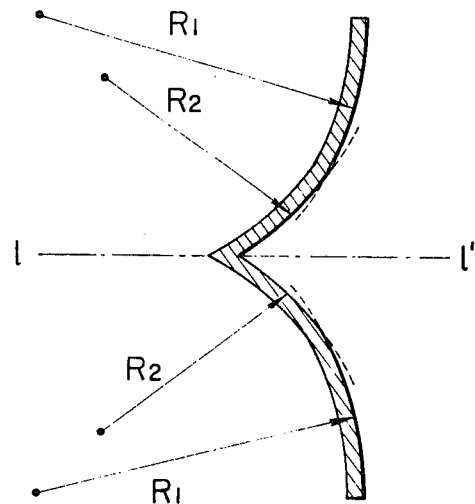

Further, in this invention, the paired arcs need not be the same, but they may be composed of a plurality of arc surfaces of different radii of curvature. By way of example, FIG. 10A shows a convex transducer in which each of the paired arc surfaces is formed of a plurality of arcs, while FIG. 10B shows a case where similar arcs are performed in an acoustic lens. In the figures, $R_1$ and $R_2$ denote the different radii of curvature.

Although, in the above, the ultrasonic source is constructed by use of the surface type transducer, this invention is not restricted to this construction. The same source as the foregoing ultrasonic sources can be realized in such way that a surface type transducer (flat disc transducer) is constructed by the use of a group of transducers in which the prior-art ring type transducers are concentrically arrayed, and that ultrasonic waves are generated from the constituent transducers with predetermined time delays.

Figure 11:
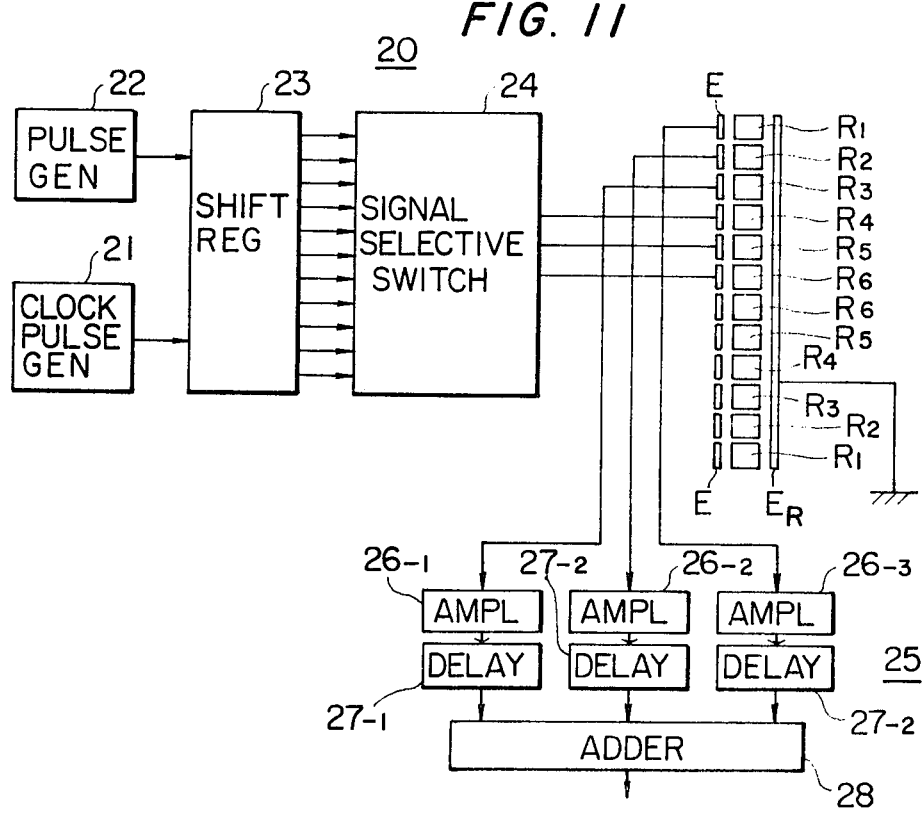
FIG. 11 is a block diagram showing the construction of still another embodiment of this invention.

FIG. 11 shows the construction of an embodiment of the ultrasonic source employing a group of transducers in which ring type transducers are concentrically arrayed. In the figure, $R_1 - R_g$ designate sections of the ring type transducers concentrically arrayed, and the transducers are arranged in the order of $R_1, R_2, R_3 \ldots$ and $R_6$ from the outermost one towards the intermost one. An electrode E is disposed on one side of each of the transducers, while a common electrode $E_R$ is disposed on the other side of the transducers. The electrode $E_R$ is grounded. Numeral 21 denotes a clock pulse generator, numeral 22 a pulse generator, numeral 23 a shift register, numeral 24 a signal selection switch, numerals 26-1 to 26-3 amplifiers, respectively, numerals 27-1 to 27-3 delay circuits, respectively, and numeral 28 an adder.

In such construction, a pulse signal generated from the pulse generator 22 becomes an input to the shift register 23. The pulse signal is provided by pulse signals with predetermined time delays by clock pulses from the clock pulse generator 21, and the latter pulse signals become outputs from the shift register 23. The output pulse signals of the shift register 23 are applied to the group of ring type transducers by the signal selection switch 24. The ring type transducers $R_1 - R_6$ are individually driven by the pulse signals selected by the signal selection switch 24. If, by way of example, sets of the ring type transducers $R_1 - R_6$, $R_2 - R_5$ and $R_3 - R_4$ are driven with the time delays in the order mentioned, the embodiment will become the same as a case where an acoustic lens exists owing to the time delays, and generated wave fronts will become similar to those produced by the transducer of FIG. 5 and accordingly by the transducer of FIG. 2A. At reception, reflected waves which the respective transducers receive are plane waves. The reflected waves can therefore be reconstructed in such way that signals generated from the respective transducers are amplified by the amplifiers 26-1, 26-2 and 26-3, that the amplified signals are delayed by the time delays by means of the delay circuits 27-1, 27-2 and 27-3, and that output signals from the delay circuits are added by the adder 28. The reconstructed waves may be displayed by conventional display means such as Braun tube.

As set forth above, according to this invention, where a fine ultrasonic beam is required over a comparatively extensive scope in fields represented by a diagnostic ultrasound equipment, the requirement can be satisfactorily met.

We claim:

1. An ultrasonic transducer device comprising ultrasonic transducer means for generating ultrasonic waves and providing a locus of points of convergence of the generated ultrasonic waves in the form of a ring, said ultrasonic transducer means including an ulrasonic transducer formed of a piezoelectric material, said ultrasonic transducer being a surface type transducer and being provided with a shape such that a locus of points of convergence of said generated ultrasonic waves forms a ring.

2. An ultrasonic transducer device according to claim 1, wherein said ultrasonic transducer is provided with a shape in the form of a body of revolution of two adjacent curved surfaces joined at the adjacent ends thereof.

3. An ultrasonic transducer device according to claim 2, wherein each curved surface has a point of convergence at its center of curvature.

4. An ultrasonic transducer device according to claim 2, wherein said ultrasonic transducer is provided with a shape such that a section of an axis thereof forms a pair of revolutionary planes consisting of said two curved surfaces.

5. An ultrasonic transducer device according to claim 2, wherein each curved surface is a concave arc surface.

6. An ultrasonic transducer device according to claim 2, wherein each curved surface is a convex arc surface.

7. An ultrasonic transducer device according to claim 2, wherein the curved surfaces are one of paraboloidal and ellipsoidal surfaces.

8. An ultrasonic transducer device according to claim 2, wherein the curved surfaces are formed of a plurality of different radii of curvature.

9. An ultrasonic transducer device comprising ultrasonic transducer means for generating ultrasonic waves and providing a locus of points of convergence of the generated ultrasonic waves in the form of a ring, said ultrasonic transducer means including an ultrasonic transducer formed of piezoelectric material, said ultrasonic transducer being a surface type plane transducer, said ultrasonic transducer means further comprising an acoustic lens bonded onto one flat surface of said plane transducer, said acoustic lens having a shape of a body of revolution of two adjacent curved surfaces joined together at the adjacent ends thereof.

10. An ultrasonic transducer device according to claim 9, wherein each curved surface has a point of convergence at its center of curvature.

11. An ultrasonic transducer device according to claim 9, wherein a section containing an axis of said acoustic lens forms a pair of revolutionary planes consisting of said curved surfaces.

12. An ultrasonic transducer device according to claim 11, wherein said acoustic lens is provided with a flat surface bonded onto the one flat surface of said plane transducer.

13. An ultrasonic transducer device according to claim 11, wherein each curved surface is a concave arc surface.

14. An ultrasonic transducer device according to claim 11, wherein each curved surface is a convex arc surface.

15. An ultrasonic transducer device according to claim 9, wherein the curved surfaces are one of paraboloidal and ellipsoidal surfaces.

16. An ultrasonic transducer device according to claim 9, wherein the curved surfaces are formed of a plurality of different radii of curvature.

* * * * *